United States Patent [19]
Tisone

[11] Patent Number: 5,743,960
[45] Date of Patent: Apr. 28, 1998

[54] PRECISION METERED SOLENOID VALVE DISPENSER

[75] Inventor: Thomas C. Tisone, Orange, Calif.

[73] Assignee: Bio-Dot, Inc., Irvine, Calif.

[21] Appl. No.: 687,712

[22] Filed: Jul. 26, 1996

[51] Int. Cl.[6] .......................... B05B 13/02; B05B 5/025
[52] U.S. Cl. ...................... 118/683; 118/305; 239/346; 239/368; 239/369; 239/371
[58] Field of Search .................................. 118/683, 300, 118/305, 313; 239/551, 585.1; 222/504

[56] References Cited

U.S. PATENT DOCUMENTS

| | | |
|---|---|---|
| 2,264,564 | 12/1941 | Connor . |
| 3,704,833 | 12/1972 | Wheat ...................................... 239/585 |
| 5,056,462 | 10/1991 | Perkins et al. ........................... 118/683 |
| 5,183,742 | 2/1993 | Omoto et al. . |
| 5,366,158 | 11/1994 | Robisch et al. . |
| 5,385,844 | 1/1995 | Kennamer et al. ..................... 436/13 |
| 5,405,050 | 4/1995 | Walsh ........................................ 222/1 |
| 5,464,739 | 11/1995 | Johnson et al. . |
| 5,509,966 | 4/1996 | Sykes ...................................... 118/697 |

OTHER PUBLICATIONS

IBC's 2nd Annual Conference on "MicroFabrication & Microfluidic Technologies, Advances in the Miniaturization of Bioanalytical Devices", Aug. 7 and 8, 1997, Renaissance Stanford Court Hotel, San Francisco, CA.

Series XY-3000 Brochure—Aug. 1994.

BioJet Specification—Sep. 1995.

Series MD-1000 Brochure—Aug. 1994.

BioDot AirJet-2000 Specification—Aug. 1994.

CV1000 Syringe Pump Dispenser—Aug. 1994.

BioDot, Inc. Brochure—Sep. 1995.

Bio-Dot, Inc. Product Catalog.

*Primary Examiner*—Donald E. Czaja
*Assistant Examiner*—Jacqueline A. Ruller
*Attorney, Agent, or Firm*—Knobbe, Martens, Olsen & Bear, LLP

[57] ABSTRACT

A reagent dispensing apparatus is provided including a positive displacement syringe pump in series with a solenoid valve dispenser. The pump is controlled by a stepper motor or the like to provide an incremental quantity or continuous flow of reagent to the solenoid valve dispenser. The solenoid valve is opened and closed in at a predetermined frequency and duty cycle to dispense droplets of reagent onto a target substrate at the metered flow rate.

34 Claims, 5 Drawing Sheets

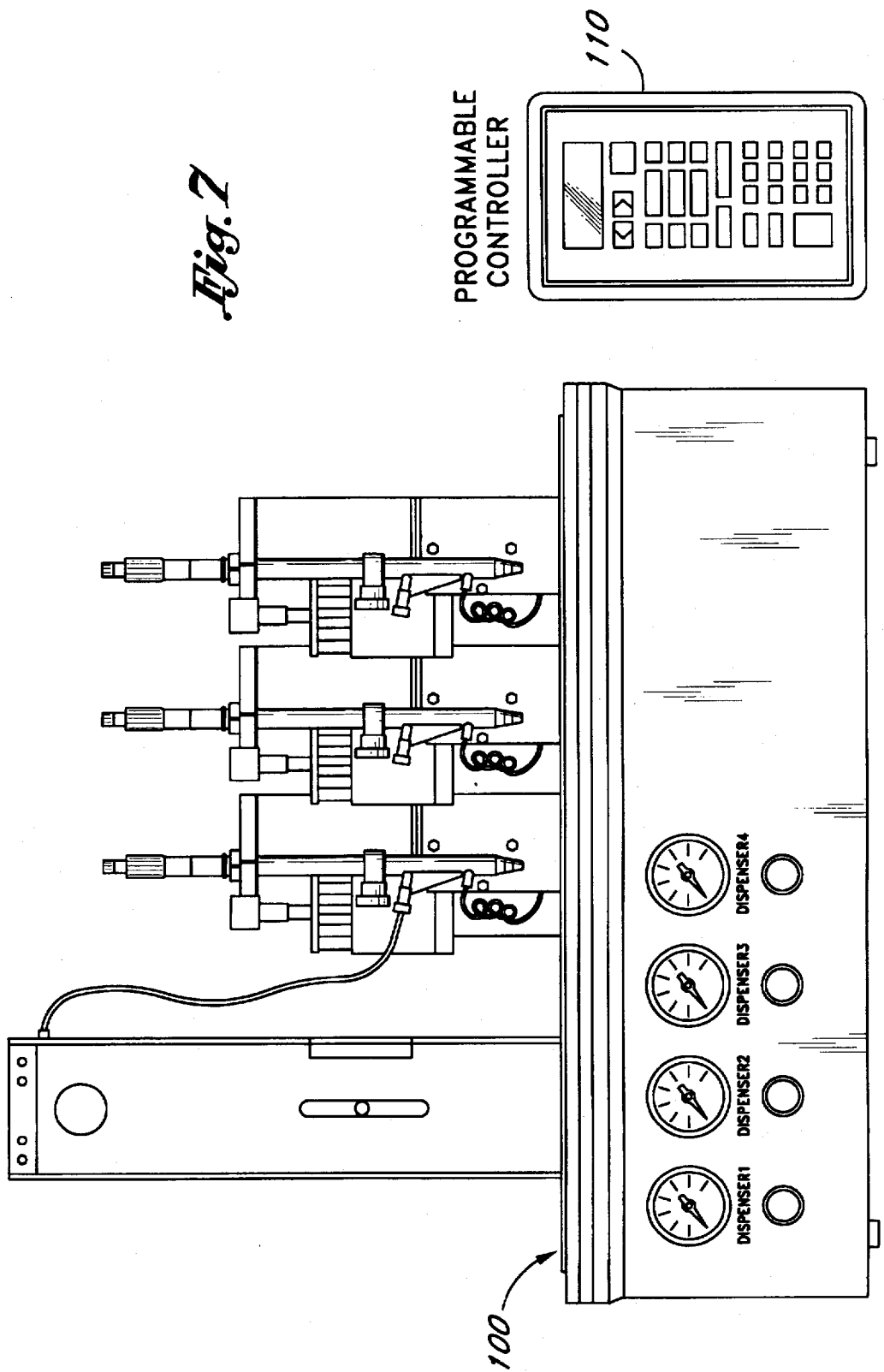

PRECISION METERED SOLENOID VALVE DISPENSER

BACKGROUND OF THE INVENTION

1. Field of the Invention

The present invention relates generally to an improved apparatus for dispensing chemical reagents onto a substrate and, in particular, to a precision metered solenoid valve dispensing system for coating precise quantities of chemical reagents onto a receptive membrane to form a diagnostic test strip.

2. Description of the Prior Art

Clinical testing of various bodily fluids conducted by medical personnel are well-established tools for medical diagnosis and treatment of various diseases and medical conditions. Such tests have become increasingly sophisticated, as medical advancements have led to many new ways of diagnosing and treating diseases.

The routine use of clinical testing for early screening and diagnosis of diseases or medical conditions has given rise to a heightened interest in simplified procedures for such clinical testing that do not require a high degree of skill or which persons may conduct on themselves for the purpose of acquiring information on a physiological relevant condition. Such tests may be carried out with or without consultation with a health care professional. Contemporary procedures of this type include blood glucose tests, ovulation tests, blood cholesterol tests and tests for the presence of human chorionic gonadotropin in urine, the basis of modern home pregnancy tests.

One of the most frequently used devices in clinical chemistry is the test strip or dip stick. These devices are characterized by their low cost and simplicity of use. Essentially, the test strip is placed in contact with a sample of the body fluid to be tested. Various reagents incorporated on the test strip react with one or more analytes present in the sample to provide a detectable signal.

Most test strips are chromogenic whereby a predetermined soluble constituent of the sample interacts with a particular reagent either to form a uniquely colored compound, as a qualitative indication of the presence or absence of the constituent, or to form a colored compound of variable color intensity, as a quantitative indication of the amount of the constituent present. These signals may be measured or detected either visually or via a specially calibrated machine.

For example, test strips for determining the presence or concentration of leukocyte cells, esterase or protease in a urine sample utilize chromogenetic esters which produce an alcohol product as a result of hydrolysis by esterase or protease. The intact chromogenetic ester has a color different from the alcohol hydrolysis product. The color change generated by hydrolysis of the chromogenetic ester, therefore provides a method of detecting the presence or concentration of esterase or protease, which in turn, is correlated to the presence or concentration of leukocyte cells. The degree and intensity of the color transition is proportional to the amount of leukocyte esterase or HLE detected in the urine. See U.S. Pat. No. 5,464,739.

The emergence and acceptance of such diagnostic test strips as a component of clinical testing and health care in general has led to the development of a number of quality diagnostic test strip products. Moreover, the range and availability of such products is likely to increase substantially in the future.

Because test strips are used to provide both quantitative and qualitative measurements, it is extremely important to provide uniformity in distribution of the reagents on the test strip substrate. The chemistry is often quite sensitive and medical practice requires that the testing system be extremely accurate. When automated systems are used, it is particularly important to ensure that the test strips are reliable and that the measurements taken are quantitatively accurate.

Application of one or more reagents to a test strip substrate is a highly difficult task. The viscosities and other flow properties of the reagents, their reactiveness with the substrate or other reagents vary from reagent to reagent, and even from lot to lot of the same reagent. It is also sometimes necessary or desirable to provide precise patterns of reagent on the test strip having predetermined reagent concentrations. For example, some test strips provide multiple test areas that are serially arranged so that multiple tests may be performed using a single test strip. U.S. Pat. No. 5,183,742, for instance, discloses a test strip having multiple side-by-side detection regions or zones for simultaneously performing various tests upon a sample of body fluid. Such test strip may be used to determine, for example, levels of glucose, protein, and the pH of a single blood sample. It is often difficult, however, to form sharp lines or other geometric shapes having uniform concentrations of reagent.

For several years the industry has been developing dispensing methods based on the use of solenoid valve dispensers such as the type used for modern ink-jet printing. These dispensers generally comprise a small solenoid-activated valve which can be opened and closed electronically at high speeds. The solenoid valve is connected to a pressurized vessel or reservoir containing the fluid to be dispensed. In operation, the solenoid is energized by a pulse of electrical current, which opens the valve for a predetermined duty-cycle or open time. This allows a small volume of liquid to be forced through the nozzle forming a droplet which is then ejected from the valve onto the target substrate. The size and frequency of the droplets and the amount of reagent flow onto the substrate is controlled by adjusting the frequency and pulse-width of energizing current provided to the solenoid valve and/or by adjusting the pressure of the reservoir.

Currently available dispensing techniques, however, are limited in the flexibility they have to independently adjust and regulate droplet size, droplet frequency and absolute flow rates of dispensed reagent. Flow rates can often drift due to changes in temperature or the viscosity of the reagent. This can cause undesirable lot to lot variances of reagent coating concentrations or coating patterns. Many reagents that are used for diagnostic testing are so reactive with the receptive membrane or substrate that large droplets can form impressions on the membrane surface at the point of initial contact before the droplets flow together to form the desired pattern. As a result, it is sometimes desirable to dispense very small droplets of reagent. Often, however, a desired droplet size or frequency is simply not attainable for a desired production flow rate. It is sometimes necessary, therefore, to perform production runs of test strips at slower than optimal speeds in order to ensure adequate results. This can increases the cost of production significantly. Solenoid valves are also susceptible to clogging by small air or gas bubbles forming in the valve itself or in the lines or conduits which supply reagent or other liquids to the dispenser. This is a major reliability problem with many conventional solenoid valve dispensers.

While some of these problems can be controlled or mitigated by adding surfactants or various other chemical additives to modify the surface tension or other flow characteristics of the droplets, compatible chemistry is not available for all reagents. Also the use of surfactants and other chemicals can often lead to other problems either in the test strip itself or in the dispensing apparatus or production processes.

SUMMARY OF THE INVENTION

The reagent dispensing apparatus of the present invention can dispense desired quantities of chemical reagents or other liquids onto a receptive membrane while providing the ability to independently and precisely adjust droplet size, droplet frequency and reagent flow rates.

In accordance with one preferred embodiment, the present invention comprises a reagent dispensing apparatus including a positive displacement syringe pump provided in series with a solenoid valve dispenser. The pump is controlled by a stepper motor or the like to provide precision incremental or continuous flow of reagent to the solenoid valve dispenser. The solenoid is selectively energized to open and close the valve at a desired frequency and/or duty-cycle, forming droplets of reagent which are then ejected onto the target substrate. Advantageously, the droplet size, droplet frequency and flow rate of the reagent can be precisely controlled independently of the particular system operating parameters of the solenoid valve dispenser. Thus, new dispensing modes are achieved having improved performance and range of operation.

In accordance with another preferred embodiment, the present invention comprises a reagent dispensing apparatus including a platform for supporting a test strip substrate or membrane and a carriage supported on the platform and adapted for X, X-Y or X-Y-Z motion relative thereto. A solenoid valve dispenser is mounted on the carriage such that it can dispense reagent in a controlled and exacting manner on the target substrate to form lines, spots or other geometric patterns, as desired. A positive displacement syringe pump is provided in series with the solenoid valve dispenser and is controlled by a stepper motor or the like to provide incremental or continuous flow of reagent to the solenoid valve dispenser. The solenoid is selectively energized to open and close the valve at a desired frequency and/or duty-cycle, forming droplets of reagent which are ejected onto the target substrate. The positive displacement syringe pump is preferably electronically controlled and may be coordinated with X, X-Y or X-Y-Z motion of the carriage so that reagent density may be input in terms of flow or volume per unit length. As a result, the present invention allows the desired input flow rate parameter to directly dictate the performance of the dispenser, rather than being determined by system parameters such as reservoir pressure, valve frequency/duty-cycle and the particular viscosity and other flow characteristics of the reagent.

In accordance with another preferred embodiment, the present invention comprises an electrostatic printing apparatus including a precision metered solenoid valve dispenser for dispensing individual droplets or a series of droplets having a predetermined size, frequency and/or flow rate. One or more positive displacement pumps is provided in series with a solenoid valve dispenser to provide precision incremental or continuous flow of one or more liquids to the solenoid valve dispenser. The solenoid is selectively energized to open and close the valve at a desired frequency and/or duty-cycle, forming droplets of reagent which are ejected from the valve. Individual droplets are then electrically charged and selectively deflected by an electric field to form a desired dot matrix pattern on the target substrate.

These and other objects and advantages of the present invention will be readily ascertainable from the following detailed description of the preferred embodiments, having reference to the attached drawings, the invention not being limited to any particular preferred embodiment.

BRIEF DESCRIPTION OF THE DRAWINGS

FIG. 7 is a front elevational view of an optional dispenser platform for use in accordance with the present invention.

DETAILED DESCRIPTION OF THE PREFERRED EMBODIMENTS

Figure 1:
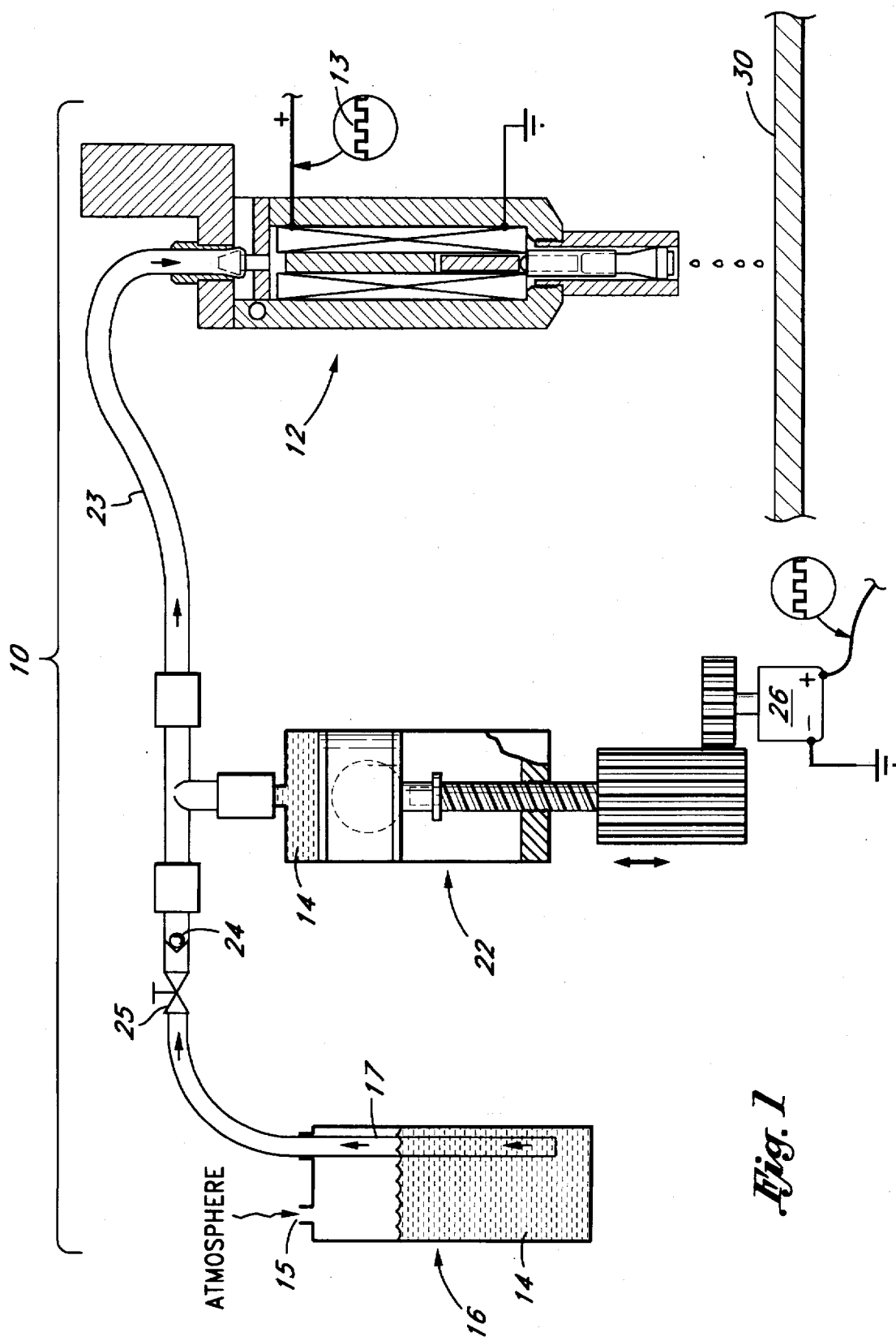
FIG. 1 is a schematic drawing of a precision metered solenoid valve dispensing apparatus having features in accordance with the present invention.

FIG. 1 is a schematic drawing of a precision metered solenoid valve dispensing apparatus 10 having features in accordance with the present invention. The dispensing apparatus 10 generally comprises a solenoid valve dispenser 12 for dispensing reagent 14 from a reservoir 16 and a positive displacement syringe pump 22 intermediate the reservoir 16 and the solenoid valve 12 for precisely metering the volume and/or flow rate of reagent dispensed. The solenoid valve dispenser 12 is energized by one or more electrical pulses 13 provided by a pulse generator 15.

Solenoid Valve Dispenser

Figure 2:
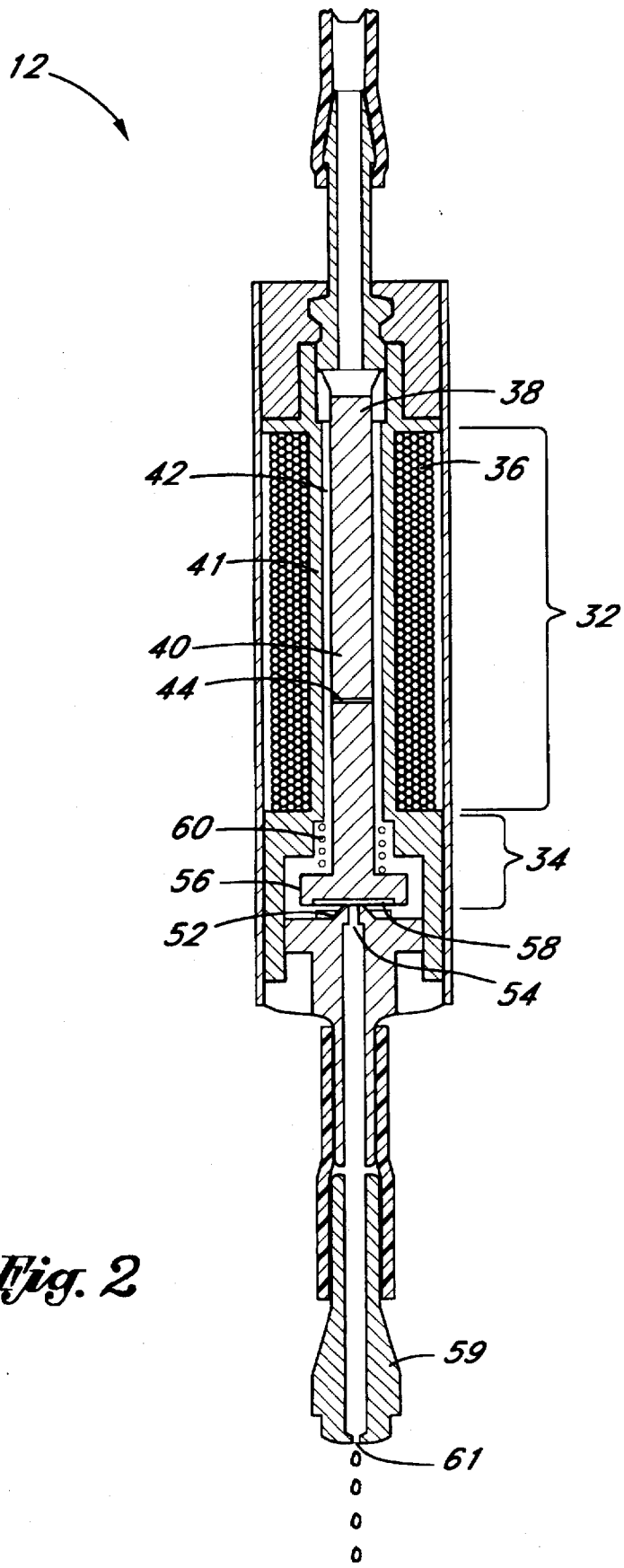
FIG. 2 is a cross-sectional view of the solenoid valve dispenser of FIG. 1.

FIG. 2 is a cross-sectional view of the solenoid valve dispenser 12, shown in FIG. 1. Solenoid valve dispensers of this type are commonly used for ink-jet printing and are commercially available from sources such as The Lee Company of Westbrook, Conn. The dispenser 12 generally comprises a solenoid portion 32 and a valve portion 34. The solenoid portion 32 comprises an electromagnetic coil or winding 36, a static core 38 and a movable plunger 40. The static core 38 and movable plunger 40 are disposed within a hollow cylindrical sleeve 41 and are preferably spaced at least slightly away from the inner walls of the sleeve 41 so as to form an annular passage 42 through which the reagent or other liquid to be dispensed may flow. The static core 38 and movable plunger 40 are preferably formed of a ferrous or magnetic material, such as iron, and are separated by a small gap 44. Those skilled in the art will appreciate that when the solenoid coil 36 is energized a magnetic field is created which draws the plunger 40 upward toward the static core 38, closing the gap 44 and opening the valve 34.

The valve portion 34 comprises a valve seat 52, having an orifice opening 54, and a stopper 56 having a valve face 58 adapted to seal against the valve seat 52. The stopper 56 is in mechanical communication with the plunger 40 and is spring biased toward the valve seat 52 via coil spring 60. Again, those skilled in the art will readily appreciate that as the plunger 40 moves up and down, the valve 34 will open and close, accordingly. Moreover, each time the valve 34 opens and closes, a volume of liquid is forced through the valve orifice 54 to form a pulse or pressure wave which ejects a droplet of liquid from the exit orifice 61 of the nozzle tip 59.

Conventionally, a pressurized reservoir (not shown) having a predetermined constant pressure is used to force liquid reagent or other liquid through the valve orifice 54 during the time interval in which the valve 34 is open. Under controlled conditions, such dispensers may have a repeatability of ±2% with a minimum drop size of about 30–35 nanoliters. The size of the droplet will be determined by system operating parameters such as the reservoir pressure, valve open time or duty-cycle, and the viscosity and other flow characteristics of the particular reagent or liquid being dispensed. Of course, certain fixed parameters, such the size and shape of the nozzle 59, will also play an important role in the operational characteristics of the valve in terms of droplet size and repeatability. In general, however, droplet size will increase with increasing reservoir pressure and valve open time.

In accordance with the present invention, however, a positive displacement pump 22 is placed in series between the supply reservoir 16 and the solenoid valve dispenser 12, as shown in FIG. 1. For a given range of flow rates the valve orifice 54 (FIG. 2) now admits a quantity and/or flow rate of reagent as determined solely by the positive displacement pump 22. For example, the flow rate could be set to deliver 1 microliter per second of reagent. The pump 22 will then deliver a steady flow of reagent to the solenoid valve dispenser 12 at the programmed rate. As the solenoid valve is opened and closed, a series of droplets will be formed at the desired volume flow rate and ejected onto the target substrate 30. This substrate is preferably a receptive membrane adapted to bond with the reagent so as to form a diagnostic test strip. Alternatively, the substrate 30 may be paper, celluous, plastic or any other wet or dry surface capable of receiving a dispensed reagent or other liquid.

Advantageously, within a certain operating range the size of the droplets can be adjusted without affecting the flow rate of reagent simply by changing the frequency of the energizing pulses 13 provided to the solenoid valve dispenser 12. Of course, there are physical limitations of valve open time or duty-cycle necessary to achieve stable droplet formation. If the open time is too short relative to the flow rate provided by the metering pump 22, the pressure will increase and possibly prevent the valve from opening or functioning properly. If the open time is too long relative to the flow rate, then drop formation may not be uniform for each open/close cycle. Nevertheless, for a given flow rate of reagent provided by the pump 22 there will be a range of compatible frequencies and/or valve open times or duty-cycles in which stable dispensing operations may be achieved at the desired flow rate and droplet size. This range may be determined experimentally for a given production set up.

As discussed in more detail below, the combination of a solenoid valve dispenser and a metering pump provides a new dimension of control which provides additional production capabilities not achievable with conventional solenoid valve dispensers. Unlike conventional solenoid valve dispensers, which typically have only a single flow rate or operating point for a given set of system operating parameters (eg. reservoir pressure, valve frequency and duty cycle), the present invention provides a range of metered flow rates that will achieve stable dispensing operation. Moreover, because the solenoid valve dispenser 12 is forced to deliver precise quantities and/or flow rates of reagent, the solenoid valve dispenser is not as susceptible to clogging due by air or gas bubbles. Rather, any air bubbles tend to be ejected out of the solenoid valve dispenser 12 by operation of the positive displacement pump 22.

Piezoelectric Dispenser

Figure 3:
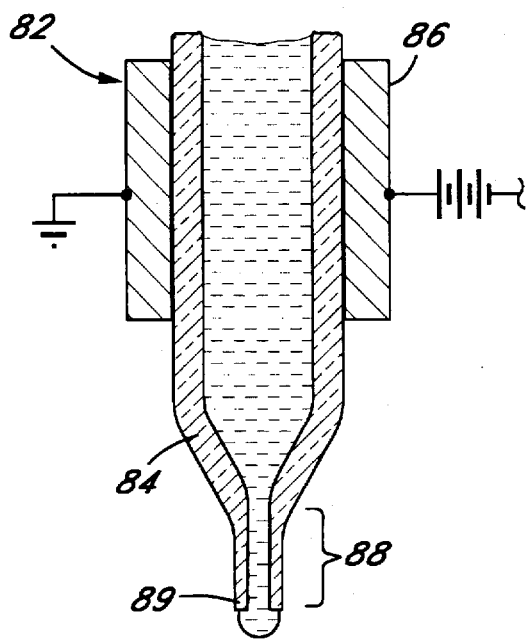
FIG. 3 is a cross-sectional view of an optional piezoelectric dispenser for use in accordance with the present invention.

FIG. 3 shows a cross-sectional view of an optional piezoelectric dispenser 82 which may also have advantageous use in accordance with the present invention as a substitute or replacement for the solenoid valve dispenser 12. The piezoelectric dispenser generally comprises a capillary tube 84 made of glass or other suitable material and a piezoelectric constrictor 86 disposed around the capillary tube 84, as shown. The capillary tube 84 has a nozzle portion 88 of a reduced diameter. When the capillary tube 84 is constricted by the piezoelectric constrictor 86, droplets 90 are formed at the exit orifice 89 of the nozzle portion 88. Advantageously, the dynamics of the piezoelectric dispenser 82 are such that it is able to operate at higher frequencies and shorter duty cycles than typical solenoid valve dispensers, resulting in even smaller droplets 90. Operation of the piezoelectric dispenser in terms of adjusting droplet size, frequency and flow rates is substantially the same as that described above and, therefore, will not be repeated here.

Syringe Pump

Figure 4:
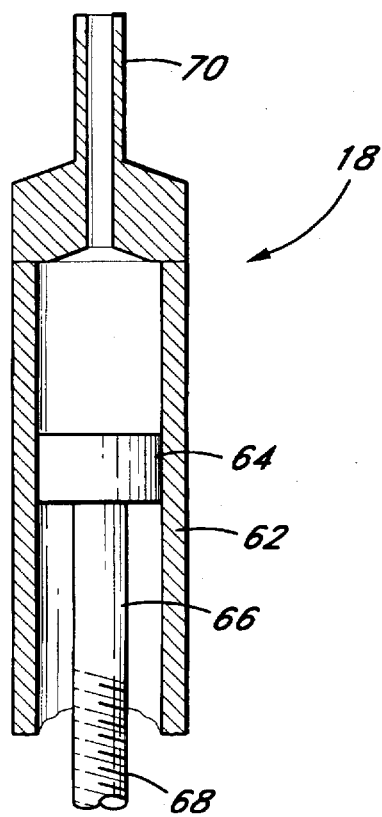
FIG. 4 is a cross-sectional detail view of the syringe pump of FIG. 1.

The positive displacement pump 22 may be any one of several varieties of commercially available pumping devices for metering precise quantities of liquid. A syringe-type pump 22, as shown in FIG. 1, is preferred because of its convenience and commercial availability. A wide variety of other pumps may used, however, to achieve the benefits and advantages as disclosed herein. These may include, without limitation, rotary pumps, peristaltic pumps, squash-plate pumps, and the like. As illustrated in more detail in FIG. 4, the syringe pump 22 generally comprises a syringe housing 62 of a predetermined volume and a plunger 64 which is sealed against the syringe housing by O-rings or the like. The plunger 64 mechanically engages a plunger shaft 66 having a lead screw portion 68 adapted to thread in and out of a base support (not shown). Those skilled in the art will readily appreciate that as the lead screw portion 68 of the plunger shaft 66 is rotated the plunger 64 will be displaced axially, forcing reagent from the syringe housing 62 into the exit tube 70. Any number of suitable motors or mechanical actuators may be used to drive the lead screw 68. Preferably, a stepper motor 26 (FIG. 1) or other incremental or continuous actuator device is used so that the amount and/or flow rate of reagent can be precisely regulated.

Suitable syringe pumps are commercially available, such as the Bio-Dot CV1000 Syringe Pump Dispenser, available from Bio-Dot, Inc. of Irvine, Calif. This particular syringe pump incorporates an electronically controlled stepper motor for providing precision liquid handling using a variety of syringe sizes. The CV1000 is powered by a single 24 DC volt power supply and is controlled via an industry-standard RS232 or RS485 bus interface. The syringe pump may have anywhere from 3,000–24,000 steps, although higher resolution pumps having 48,000 steps or more may also be used to enjoy the benefits of the invention herein disclosed. Higher resolution pumps, such as piezoelectric pumps, may also be used to provide even finer resolutions as desired. The lead screw 68 may optionally be fitted with an optical encoder or similar device to detect any lost steps. Alternatively, the lead screw of the metering pump can be replaced with a piezoelectric slide to provide both smaller volume increments and also faster acceleration/deceleration characteristics. Multiple syringe pumps may also be used in parallel, for example, for delivering varying concentrations of reagent and/or other liquids to the dispenser or for alternating dispensing operations between two or more reagents. This could have application, for instance, to ink jet printing using one or more colored inks or liquid toners.

The travel of the plunger 64 is preferably about 60 mm. Plunger speeds may range from 0.8 seconds per stroke with a 10-step minimum for low-resolution pumping or 1.5 seconds per stroke with a 20-step minimum for high-speed resolution pumping. The stroke speed may vary depending upon the syringe size and the tubing used. Syringes may vary from less than 50 microliters to 25 milliliters, or more as needed. For most reagent dispensing applications it should be adequate to provide a syringe having a volume from about 500 microliters to about 25 milliliters. The minimum incremental displacement volume of the pump will depend on the pump resolution and syringe volume. For example, for a syringe housing volume of 500 microliters and 12,000 step resolution pump the minimum incremental displacement volume will be about 42 nanoliters. Minimum incremental displacement volumes from about 2.1 nanoliters to 2.1 milliliters are preferred, although higher or lower incremental displacement volumes may also be used while still enjoying the benefits of the present invention. For example, 0.42 nanoliters to about 2.1 microliters may also be used.

The syringe housing 62 may be made from any one of a number of suitable bio compatible materials such as glass, Teflon™ or Kel-F. The plunger 64 is preferably formed of virgin Teflon™. Referring to FIG. 1, the syringe is connected to the reservoir 16 and the solenoid valve dispenser using a Teflon tubing 23, such as ¼-inch O.D. tubing provided with luer-type fittings for connection to the syringe and dispenser. Various check valves 24 or shut-off valves 25 may also be used, as desired or needed, to direct the flow of reagent to and from the reservoir 16, syringe pump 22 and dispenser 12.

Reagent Reservoir

The reagent reservoir 16 may be any one of a number of suitable receptacles capable of allowing a liquid reagent 14 to be siphoned into pump 22. The reservoir may be pressurized, as desired, but is preferable vented to the atmosphere, as shown, via a vent opening 15. The particular size and shape of the reservoir 16 is relatively unimportant.

A siphon tube 17 extends downward into the reservoir 16 to a desired depth sufficient to allow siphoning of reagent 14. Preferably the siphon tube 17 extends as deep as possible into the reservoir 16 without causing blockage of the lower inlet portion of the tube 17. Optionally, the lower inlet portion of the tube 17 may be cut at an angle or have other features as necessary to desirable to provide consistent and reliable siphoning of reagent 14.

Operation

As indicated above, a key operational advantage achieved by the present invention is that over a certain range the flow of reagent is substantially independent of the particular flow characteristics of the reagent and operating parameters of the solenoid valve dispenser 12. For example, the size of droplets formed by the dispenser can be adjusted without affecting the flow rate of reagent metered by the pump by changing the operating frequency of the solenoid valve dispenser 12. The quantity or flow rate of reagent dispensed is substantially unaffected because it is precisely controlled by the positive displacement pump 22. This has particular advantage, for example, in applications requiring the dispensing of very small droplets or for dispensing higher viscosity reagents, since the reagent flow can be precisely controlled without substantial regard to the system operating parameters otherwise required to achieve stable dispensing operations.

For example, with a conventional solenoid valve dispenser in order to obtain very small droplets, one must attempt to shorten the open time or duty cycle of the valve. However, as the valve open time is shortened, the flow rate of reagent decreases such that the cycle frequency of the valve must be increased to compensate. At a certain point the flow characteristics of the reagent will limit the ability to achieve uniform formation of droplets when the valve open time is very small.

Moreover, even if stable dispensing operation could be achieved by increasing the reservoir pressure, such increased pressure will tend to increase the droplet size and flow rate of reagent, necessitating even further adjustments to achieve stable dispensing operation at the desired flow rate and droplet size.

The present invention, however, overcomes these and other problems of the prior art by precisely metering the quantity and/or flow rate of the reagent. Advantageously, the amount of reagent can be precisely regulated over a wide range without being substantially affected by the particular operating parameters of the solenoid valve dispenser. This feature enables valve frequency, droplet size and flow rates to be varied dramatically from one range to another. Thus, the present invention not only provides precise metering of reagent, but also adds a new dimension of operation of the solenoid valve dispenser not before possible.

Another important operational advantage is that droplet sizes attainable with the present invention are much smaller than those achieved with conventional solenoid valve dispensers. The present invention is capable of attaining minimum stable droplet sizes in the range of 1–4 nanoliters, compared with 30–35 nanoliters for most conventional solenoid valve dispensers. In principle, even smaller droplet sizes (on the order of 0.54 nanoliters or smaller) should be attainable in accordance with the present invention using syringe pumps having a resolution of 48,000 steps and a syringe volume of 25 microliters. Drop formation experiments have demonstrated the ability to dispense 4.16-nanoliter drops with very good repeatability using a nozzle 59 (FIG. 2) having an exit orifice 61 of about 175 microns in diameter. A smaller exit orifice 61 having a diameter in the range of 75–125 microns should provide stable formation and dispensing of even smaller droplets in accordance with the present invention.

This feature of the present invention has particular advantage for high production manufacturing and processing of diagnostic test strips. In certain production applications, for example, it may be desirable to dispense very small droplets of reagent to provide optimal coating characteristics. At the same time, it may be desirable to provide high reagent flow rates for increased production levels. Typically, with a conventional solenoid valve dispenser, to increase the output flow rate the valve frequency or the length of the valve open time must be increased. But the longer the valve open time is, the larger the droplets will be. There is also an operational limit to how short the open time of the valve can be and how high the operating frequency can be will still attaining stable operation. Again, conventional solenoid valve dispensers reach their lower limit of operational stability at droplet sizes approaching 30–35 nanoliters. The present invention, however, allows the use of much shorter valve open times to attain stable operation at high flow rates by positively displacing the reagent through the valve opening. In other words, the flow of reagent is not substantially affected by the particular operating frequency of the valve or the length of the open time. It is dependent only on the displacement of the syringe pump, which acts as the forcing function for the entire system.

Of course, as noted above, there will be a maximum range of operation for a given operating frequency and valve open time. The higher limit will be the maximum amount of reagent that can be forced through the valve at maximum design pressure for the given operating frequency and valve open time. The lower limit will be determined by the stability of droplet formation. If the valve open time and/or operating frequency are too small for a given flow rate, the pressures in the dispenser will become too great, causing possible rupture or malfunction of the system. If the valve open time and/or operating frequency are too large for a given flow rate, the drop formation may not be uniform for each open/close cycle. Nevertheless, for a given flow rate of reagent provided by the pump 22 there will be a range of compatible frequencies and/or valve open times for which stable operation may be achieved. This range may be determined experimentally by adjusting the operating frequency and open time of the valve to achieve stable droplet formation.

In a particularly preferred mode of operation, the dispensing apparatus may be integrated to an X, X-Y, or X-Y-Z platform wherein the programmed motion control can be coordinated with the metering pump to deliver a desired volume per unit length, with the ability to also independently control the frequency and droplet size of the reagent being dispensed. For example, it is possible to deliver reagent at a rate of 1 microliter per centimeter at a constant table speed with a droplet size ranging between 4 and 100 nanoliters. The droplet size for a given dispenser flow rate can be controlled by adjusting the operation frequency of the solenoid valve. In this context, there are several particularly desirable modes of operation: (1) line or continuous dispensing; (2) spot or "dot" dispensing; (3) aspirating; and (4) dot matrix printing. Each of these preferred modes of operation is addressed below:

Continuous Dispensing

In the continuous dispensing mode, the metering pump is set to a prescribed flow rate to deliver a metered volume of reagent in volume-per-unit time. For example, the flow rate could be programmed to deliver 1 microliter per second. The syringe will then pump reagent to the solenoid valve 12 at the predetermined rate. By opening and closing the valve during this flow, droplets will be formed according to the open time and operating frequency of the valve. Thus, in the continuous dispensing mode, the system is not only capable of delivering precise metered flow rates of reagent, but this can be done with independent control of table speed, reagent concentration per unit length and droplet size.

Figure 5:
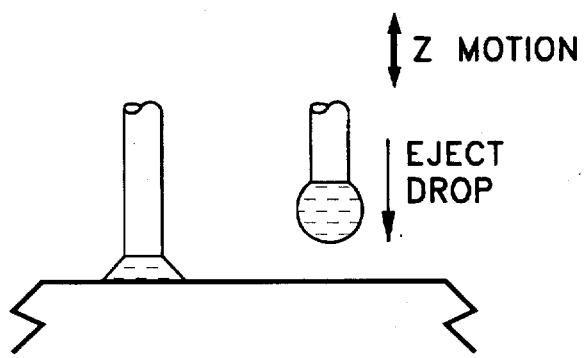
FIG. 5 is a schematic drawing illustrating two possible modes of operation of a dispenser in accordance with the present invention.

If the solenoid valve dispenser is placed very close to the substrate, as shown in FIG. 5 (to the left), then reagent will flow directly onto the substrate providing either a continuous line. This mode of continuous operation may provide particular advantage where reagent patterns having very sharp lines are necessary or desirable. If desired, a continuous drive reagent pump may also be used to assure a steady flow of reagent to the solenoid valve dispenser. More commonly, however, the solenoid valve dispenser will be spaced at least slightly away from the substrate, as shown in FIG. 5 (to the right). In this mode, discreet droplets will be formed which are ejected onto the substrate to form the desired pattern. The size of each droplet will determine the effective resolution of the resulting pattern formed on the substrate. It is convenient to express this resolution in terms of dots per inch or "dpi". The present invention should be capable of achieving dispensing resolutions in the range of 300–600 dpi or higher.

Dot Dispensing

In the dot dispensing mode, individual droplets can be dispensed at preprogrammed positions. This can be accomplished by synchronizing the solenoid valve and displacement pump with the X, X-Y or X-Y-Z platform. The metering pump is incremented to create a hydraulic pressure wave. The solenoid valve is coordinated to open and close at predetermined times relative to the pump increment. The valve may be initially opened either be before or after the pump is incremented. While the valve is open the pressure wave pushes a volume of fluid down the nozzle forming a droplet at the exit orifice at the time of peak pressure amplitude. The droplet will have a size determined by the incremental volume provided by the metering pump. For example, a 50-microliter syringe pump with a 12,000 step resolution will provide an incremental displacement volume of 4.16 nanoliters.

The timing and duration of each valve cycle relative to the hydraulic pressure wave created by the pump can be determined experimentally to achieve stable dispensing operation having the desired droplet size. If the wavelength of the hydraulic pressure wave is too large relative to the valve open time, the pressure wave may actually force the valve shut. If the wavelength is about equal to or shorter than the valve open time, then a pulse of fluid will be displaced forming a droplet. Again, the size or volume of the droplet will be determined primarily by the incremental displacement volume of the syringe pump.

If the valve open time is large relative to the pressure wavelength then several pulses or displacements may travel through the valve during the time in which it is open. This may be acceptable or even desirable for some applications, such as where bursts of droplets are desired at a programmed valve frequency. For example, the dispensing apparatus can be programmed to produce 10 drops at 100 Hz to yield a composite drop size of about 41.6 nanoliters. This mode of operation can provide the ability to dispense drop sizes down to less than 1 nanoliter with the appropriate nozzle design. It will depend on the resolution of the metering pump and the minimum valve open/close time and the size of the exit orifice. If the valve is left open too long, however, then the system may not maintain enough pressure to eject droplets. To achieve the most stable dispensing operation, the valve open time should be about consistent with the droplet volume or composite droplet volume dispensed.

The timing, frequency and duty cycle of the solenoid valve relative to the syringe pump and movable carriage/platform can be coordinated or synchronized by any one of a number controllers well known in the art. Typical controllers are microprocessor based and provide any one of a number of output control pulses or electrical signals of predetermined phase, pulse width and/or frequency. These signals may be used, for example, to control and coordinate the syringe pump, movable carriage/platform and solenoid valve dispenser in accordance with the present invention.

There may also be some optimum phasing of the pressure pulse relative to the open/close times of the solenoid valve. Stable operation has been observed, for instance, when the valve open time is adjusted to be an even multiple of the pulse width of the pump increment, with the open/close time of the valve being synchronized to be in phase with the resulting pressure wave. For example, with a 50-microliter syringe pump operating at 12,000-step resolution, the incremental displacement volume will be about 4.16 nanoliters. Therefore, stable operation should be possible with droplet sizes of some multiple of 4.16 nanoliters. The minimum droplet size for stable operation may be increased or decreased accordingly by adjusting the resolution of the pump or by increasing the size of the syringe. For a large droplet, say 9×4.16 nanoliters=33.28 nanoliters, it may be preferred to open the valve longer than for smaller droplets in order to get more uniform lines and stable operation. Again, the range of stable operation can be readily determined experimentally for each desired operating mode.

Aspirating

Another preferred mode of operation is aspirating ("sucking") precise quantities of reagent or other liquids from a sample or reservoir. This mode may be used, for example, in a "suck and spit" operation whereby a precise quantity of fluid is aspirated from one vial containing a sample fluid and then dispensed into another vial or onto a diagnostic test strip for testing or further processing. The dispenser/aspirator may be a simple nozzle or needle ("aspirating tube") or, more preferably, it may be a solenoid valve dispenser. The metering pump and dispenser/aspirator are preferably synchronized or coordinated with an X, X-Y or X-Y-Z movable platform.

In operation the metering pump is filled with a wash fluid such as distilled water. The tip of the dispenser or aspirating tube is placed into the fluid to be aspirated and the metering pump is decremented to draw a precise quantity of the fluid into the tip of the dispenser or aspirating tube. It is generally desirable to only aspirate a small volume of reagent into the tip of the solenoid valve dispenser that does not pass into the valve. The metering pump is then incremented to dispense a precise portion of the fluid into a receiving receptacle or substrate. The remaining fluid is dispensed into a waste/wash receptacle along with a predetermined quantity of the wash. This ensures that the fluid sample does not get diluted with the wash fluid and the sample is flushed out after each aspirate and dispense cycle.

This mode of operation has particular advantage for dispensing high viscosity reagents. Conventional solenoid valve dispensers typically do not work very well with solutions having a viscosity above about 5 centipoise. But there are many applications where it is desirable to dispense reagents having high viscosities. Advantageously, the present invention, when used in the aspirate/dispense mode, provides a solution to this problem. Again, in the aspirate/dispense mode the system will be filled with a wash fluid such as water or a water-based solution having a low viscosity. The reagent is first aspirated then dispensed, followed by washing of the valve by dispensing excess wash fluid.

In the case of a viscous reagent, the present invention can aspirate and dispense such reagents very effectively by decreasing the speed of aspiration. This allows more time for the more viscous fluid to flow into the tip of the solenoid valve dispenser or aspirating tube. Because the viscous fluid will then be hydraulically coupled to the wash fluid, it can now be dispensed from the nozzle effectively, since the system is driven by positive displacement and the fluids are incompressible. Using this mode, the present invention can dispense reagents of a viscosity that cannot typically be directly dispensed.

Printing

Another possibly desirable mode of operation may be to use the drop dispensing capability of the present invention in conjunction with electrostatic or dot matrix printing techniques to create printed patterns, lines and other geometric shapes on a substrate. In this case the metering pump may be used as an internal forcing function to control quantitatively the droplet size of each dot in a matrix pattern. By superimposing programmed dispensing frequency function and selective charging and deflecting of droplets, the present invention can provide drop-on-demand printing having extended capabilities for finer dot sizes and printing resolution.

Figure 6:
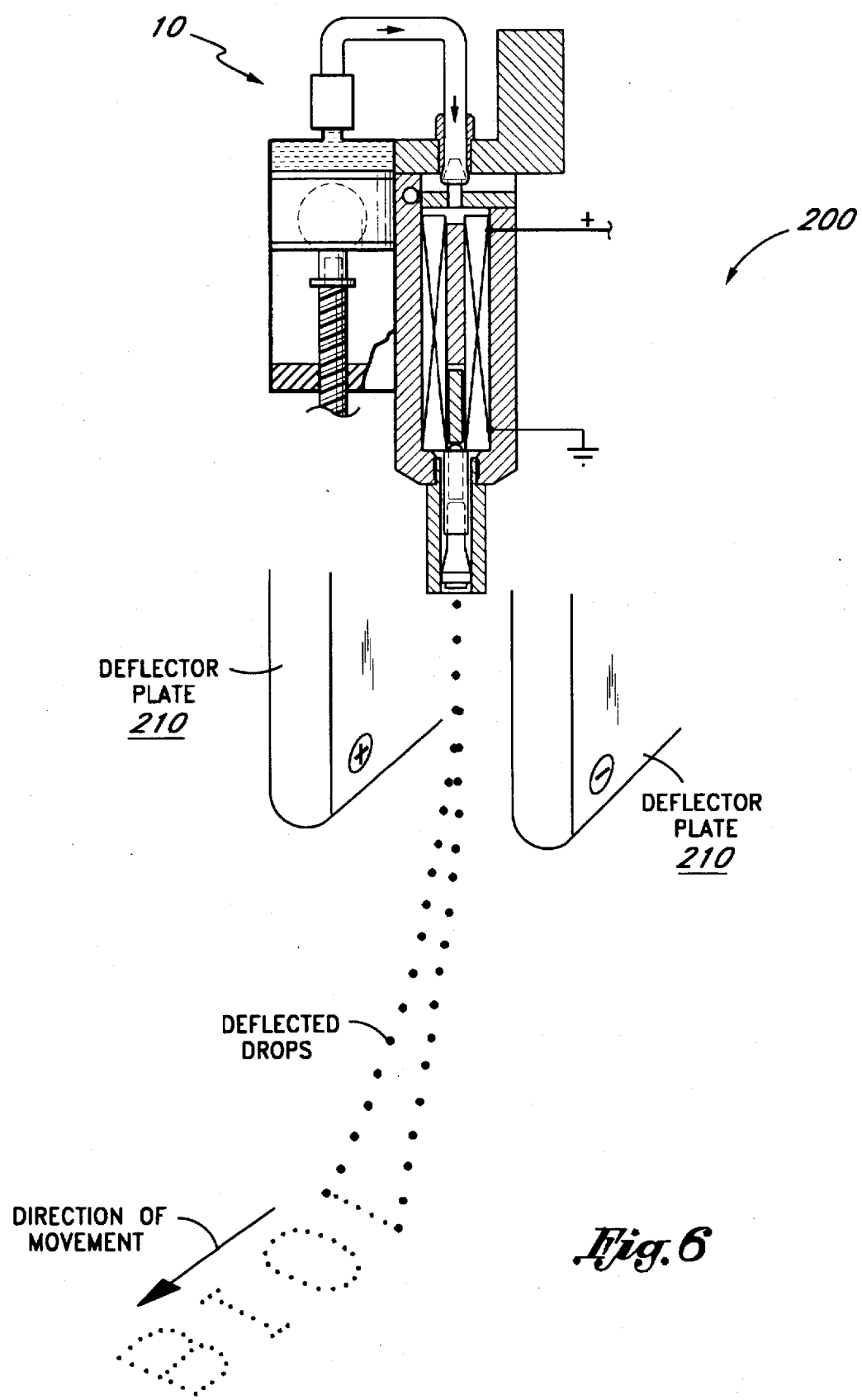
FIG. 6 is a schematic view of an electrostatic printer having features in accordance with the present invention.

For example, a dispensing apparatus 10 of present invention may be in used in conjunction with an electrostatic printing head 200, such as shown in FIG. 6 to create a dot matrix pattern on a substrate. The dispensing apparatus can be programmed to dispense droplets of a predetermined size and frequency pattern. These droplets can be electrically charged such that they may be deflected by an electric field generated between a pair of deflector plates 210. The amount of charge put on a droplet is variable, and thus, the amount of deflection is also variable. The electronics may be arranged so that droplets can be placed in any number of predetermined positions. Selective charging and deflecting of individual droplets may be used to form a desired dot matrix pattern, as shown. Alternatively, multiple dispensers and pumps may be arranged to form an array of drop-on-demand dispensers for simple dot matrix printing.

Dispensing Platforms

As noted above, the dispensing apparatus in accordance with the present invention may also be mounted on any one of a number of membrane placement and handling modules. For instance, a single platform 100 may be used to mount multiple dispensers to handle one or more reagents, as shown in FIG. 7. Such dispensing platforms may be microprocessor-based and are preferably controlled through an industry standard input/output I-O controller (not shown), such as an RS232 interface. A remote programmable controller 110 may also be used, as desired, to control the various dispensing equipment and platforms or to program a central I/O controller. The invention is also well suited for use with individual membrane strip handling modules and continuous reel-to-reel handling modules. An individual membrane strip module may incorporate an X-Y table motion for dispensing. The reel-to-reel platform may incorporate constant-speed membrane transport with mountings attached for motion of one or more dispensers. A drying oven (not shown) may also be used to increase production throughput, as desired.

It will be appreciated by those skilled in the art that the dispensing apparatus of the present invention can be used to dispense a wide variety of liquids, reagents and other substances. Although the invention has been disclosed in the context of certain preferred embodiments, those skilled in the art will readily appreciate that the present invention extends beyond the specifically disclosed embodiments to other alternative embodiments of the invention. Thus, it is intended that the scope of the invention should not be limited by the particularly disclosed embodiment described above, but should be determined only by reference to the claims that follow.

What is claimed is:

1. An apparatus for forming a diagnostic test strip comprising:

a carriage for movably supporting a receptive membrane, a non-contact solenoid valve dispenser mounted in juxtaposition with said carriage and having a valve adapted to be opened and closed at a predetermined frequency and duty cycle to form droplets of reagent which are deposited onto said receptive membrane, said droplets having a size in the range from about 0.42 nonoliters to about 2.1 microliters; and a positive displacement pump in fluid communication with a source of said reagent and said solenoid valve dispenser for metering predetermined quantities of said reagent to said solenoid valve dispenser so that the quantity and/or flow rate of said reagent dispensed by said solenoid valve dispenser can be precisely metered substantially without being affected by the particular operating parameters of said solenoid valve dispenser or the particular flow characteristics of said airborne reagent being dispensed.

2. An apparatus for dispensing precise quantities of liquid onto a substrate, comprising:

a non-contact dispenser having a valve adapted to be opened and closed at a predetermined frequency and duty cycle to form droplets of said liquid which are deposited onto said substrate and a positive displacement pump in hydraulic communication with said dispenser for metering predetermined quantities of said liquid to said dispenser:

whereby the quantity and/or flow rate of liquid dispensed by said dispenser can be precisely metered substantially without being affected by the particular operating parameters of said dispenser or the flow characteristics of said liquid being dispensed.

3. The dispensing apparatus of claim 2 wherein said liquid comprises a chemical reagent.

4. The dispensing apparatus of claim 2 wherein said valve is actuated via an electric solenoid.

5. The dispensing apparatus of claim 2 wherein said valve is actuated via a piezoelectric constrictor device.

6. The dispensing apparatus of claim 2 wherein said positive displacement pump comprises a syringe pump having a syringe housing, a plunger axially displaceable within said syringe housing and plunger shaft having a lead screw formed thereon.

7. The dispensing apparatus of claim 6 wherein said lead screw is sized and positioned such that when said lead screw is rotated, said plunger is displaced axially, causing a predetermined quantity of said liquid to be delivered to said solenoid valve dispenser.

8. The dispensing apparatus of claim 7 wherein said housing has a volume of between about 25 microliters about 25 milliliters.

9. The dispensing apparatus of claim 2 wherein said positive displacement pump comprises a stepper motor adapted to cause said pump to dispense predetermined incremental quantities of said liquid to said solenoid valve dispenser.

10. The dispensing apparatus of claim 9 wherein said positive displacement pump has an incremental displacement volume of between about 0.42 nanoliters and 2.1 microliters.

11. The dispensing apparatus of claim 9 wherein said positive displacement pump has an incremental displacement volume of less than about 4.2 nanoliters.

12. The dispensing apparatus of claim 2 wherein said positive displacement pump has a resolution of between about 3,000 and 48,000 steps.

13. The dispensing apparatus of claim 11 wherein said positive displacement pump has a resolution of at least about 12,000 steps.

14. An apparatus for dispensing a liquid onto a substrate, comprising:

a solenoid valve dispenser having a valve adapted to be opened and closed at a predetermined frequency and duty cycle to form airborne droplets of said liquid which are deposited onto said receptive membrane;

a positive displacement pump in fluid communication with said solenoid valve dispenser for metering a predetermined quantity or flow rate of said liquid to said solenoid valve dispenser; and means for independently adjusting any one of several operating parameters of said solenoid valve dispenser, including valve operating frequency and duty cycle, without substantially affecting said metered quantity or flow rate of said liquid dispensed onto said substrate.

15. The dispensing apparatus of claim 14 wherein said liquid comprises a chemical reagent and said substrate comprises a diagnostic test strip membrane.

16. The dispensing apparatus of claim 14 wherein said adjustment means comprises a programmable controller for generating pulses of electrical current or voltage of predetermined frequency and pulse width for energizing said solenoid valve dispenser.

17. The dispensing apparatus of claim 14 wherein said positive displacement pump comprises a syringe pump comprising a syringe housing, a plunger axially displaceable within said syringe housing and plunger shaft having a lead screw formed thereon.

18. The dispensing apparatus of claim 17 wherein said lead screw is sized and positioned such that when said lead screw is rotated, said plunger is displaced axially, causing a predetermined quantity of said liquid to be delivered to said solenoid valve dispenser.

19. An apparatus for aspirating or dispensing a liquid, comprising:

a carriage mounted on said platform and being adapted for X, X-Y or X-Y-Z motion relative to said platform;

a solenoid valve dispenser having a valve adapted to be opened and closed at a predetermined frequency and duty cycle;

a positive displacement pump in fluid communication with said solenoid valve dispenser for metering predetermined quantities of said liquid to or from said solenoid valve dispenser;

whereby the quantity and/or flow rate of said liquid dispensed or aspirated by said solenoid valve dispenser can be precisely metered substantially without regard to the particular operating parameters of said solenoid valve or the particular flow characteristics of said liquid to be dispensed or aspirated.

20. A printing apparatus, comprising:

a platform for supporting a substrate;

a carriage mounted on said platform and being adapted for X, X-Y or X-Y-Z motion relative to said platform;

a non-contact dispenser having a valve adapted to be opened and closed at a predetermined frequency and duty cycle to form droplets of ink, liquid toner or other liquid which are deposited onto said substrate in accordance with a predetermined desired matrix position or pattern; and a positive displacement pump in hydraulic communication with said dispenser for metering predetermined quantities of said ink, toner or other liquid to said solenoid valve dispenser.

21. The printing apparatus of claim 20 wherein said valve is actuated via an electric solenoid.

22. The printing apparatus of claim 20 wherein said valve is actuated via a piezoelectric constrictor device.

23. The printing apparatus of claim 20 comprising an array of dispensers and positive displacement pumps arranged in a desired pattern suitable for attaining a desired print matrix or pattern.

24. The printing apparatus of claim 20 further comprising an electrostatic printer head for selectively charging said droplets with a predetermined electrical charge and for deflecting said charged droplets to impact said substrate in accordance with said predetermined desired matrix position or pattern.

25. The dispensing apparatus of claim 2 in combination with a platform for supporting said substrate and a carriage mounted on said platform and being adapted for X, X-Y or X-Y-Z motion relative to said platform and wherein said solenoid valve dispenser is mounted in juxtaposition with said carriage and/or said platform.

26. The dispensing apparatus of claim 25 further comprising a controller in communication with said positive displacement pump and said carriage for coordinating the output of said pump with the relative movement of said carriage so that said liquid may be dispensed in precise quantities of flow per unit length of said substrate.

27. The dispensing apparatus of claim 14 in combination with a platform for supporting said substrate and a carriage mounted on said platform and being adapted for X, X-Y or X-Y-Z motion relative to said platform and wherein said solenoid valve dispenser is mounted in juxtaposition with said carriage and/or said platform.

28. The dispensing apparatus of claim 27 further comprising a controller in communication with said positive displacement pump and said carriage for coordinating the output of said pump with the relative movement of said carriage so that said liquid may be dispensed in precise quantities of flow per unit length of said substrate.

29. An apparatus for forming a diagnostic test strip comprising:

a support carriage and/or platform for movably transporting a receptive substrate;

a pump for metering a predetermined quantity or flow rate of liquid reagent to be dispensed;

a non-contact dispenser for receiving said metered quantity or flow rate of liquid reagent and forming airborne droplets of said liquid for depositing on said receptive substrate, said droplets having a size in the range from about 0.42 nanoliters to about 2.1 microliters; and means for regulating the metering of said predetermined quantity or flow rate of liquid reagent and the transporting of said receptive substrate such that the dispensing of said reagent may be controlled in terms of volume of reagent per unit length of substrate substantially independently of the particular operating characteristics of said dispenser and the flow characteristics of said liquid reagent being dispensed.

30. The apparatus of claim 28 wherein said pump comprises a positive displacement pump.

31. The apparatus of claim 30 wherein said positive displacement pump comprises a syringe pump.

32. The apparatus of claim 28 further comprising a stepper motor adapted to cause said pump to dispense predetermined incremental quantities of said liquid to said dispenser.

33. The apparatus of claim 28 wherein said regulating means comprises a programmable controller in communication with said pump and said carriage for coordinating the output of said pump with the relative movement of said carriage so that said liquid reagent may be dispensed in quantities of volume per unit length of said substrate.

34. The apparatus of claim 28 wherein said dispenser comprises a valve adapted to be opened and closed in accordance with a predetermined frequency and duty cycle to form droplets of a desired size and/or frequency at said predetermined quantity or flow rate.

* * * * *

UNITED STATES PATENT AND TRADEMARK OFFICE
CERTIFICATE OF CORRECTION

PATENT NO. : 5,743,960
DATED : April 28, 1998
INVENTOR(S) : Thomas C. Tisone It is certified that error appears in the above-identified patent and that said Letters Patent is hereby corrected as shown below:

In Column 13, Line 13 please replace "said airborne reagent" with --said reagent--.

In Column 13, Line 20 please replace "substrate and" with --substrate; and--.

In Column 13, Line 23 please replace "dispenser:" with --dispenser;--.

In Column 14, Line 34 please replace "comprising: a carriage mounted on said platform and being adapted for X, X-Y or X-Y-Z motion relative to said platform; a solenoid" with --comprising: a solenoid--.

Signed and Sealed this

Ninth Day of March, 1999

*Attest:*

Q. TODD DICKINSON

*Attesting Officer*  *Acting Commissioner of Patents and Trademarks*